United States Patent
Legay

(10) Patent No.: US 6,907,290 B2
(45) Date of Patent: Jun. 14, 2005

(54) MEASUREMENT OF THE COMPLEX IMPEDANCE OF AN IMPLANTABLE LEAD

(75) Inventor: Thierry Legay, Fontenay-les-Briis (FR)

(73) Assignee: ELA Medical S.A., Montrouge (FR)

( * ) Notice: Subject to any disclaimer, the term of this patent is extended or adjusted under 35 U.S.C. 154(b) by 349 days.

(21) Appl. No.: 10/033,692

(22) Filed: Dec. 21, 2001

(65) Prior Publication Data

US 2002/0123773 A1 Sep. 5, 2002

(30) Foreign Application Priority Data

Dec. 22, 2000 (FR) .......................................... 00 16906

(51) Int. Cl.⁷ .............................................. A61N 1/08
(52) U.S. Cl. .............................. 607/28; 607/8; 600/547
(58) Field of Search ................... 607/8, 27–29; 600/547

(56) References Cited

U.S. PATENT DOCUMENTS

| | | | |
|---|---|---|---|
| 4,683,417 A | | 7/1987 | De Burgat et al. ....... 324/60 C |
| 5,201,865 A | * | 4/1993 | Kuehn ........................... 607/8 |
| 5,431,692 A | * | 7/1995 | Hansen et al. .............. 607/28 |
| 5,814,088 A | * | 9/1998 | Paul et al. .................. 607/28 |
| 6,058,325 A | * | 5/2000 | Baura ............................ 607/8 |
| 6,304,781 B1 | * | 10/2001 | Busch et al. ................ 607/28 |
| 6,522,924 B1 | * | 2/2003 | Meier .......................... 607/28 |

FOREIGN PATENT DOCUMENTS

WO 99/58192 11/1999 ............ A61N/1/37

* cited by examiner

Primary Examiner—Kennedy Schaetzle
Assistant Examiner—Kristen Mullen
(74) Attorney, Agent, or Firm—Orrick Herrington & Sutcliffe, LLP

(57) ABSTRACT

A process for the measurement of the complex impedance of a lead for an active implantable medical device, in particular a pacemaker, defibrillator and or cardiovertor. This process includes the steps of producing a stimulation pulse by the discharge on the lead (10) of a tank-capacitor (22) of the device (20), charged beforehand to a given voltage level; measuring the voltage variation (V(t)) at the terminals of the tank-capacitor during the discharge; and determining the lead impedance (Zs) from the voltage thus measured. The measurement stage includes sampling at least three successive values of the voltage at the terminals of the tank capacitor, and the determining stage includes the separate determination of the resistive (Rs) and/or capacitive (CH) components of the complex impedance of the lead from the aforesaid at least three sampled values of voltage thus obtained.

8 Claims, 1 Drawing Sheet

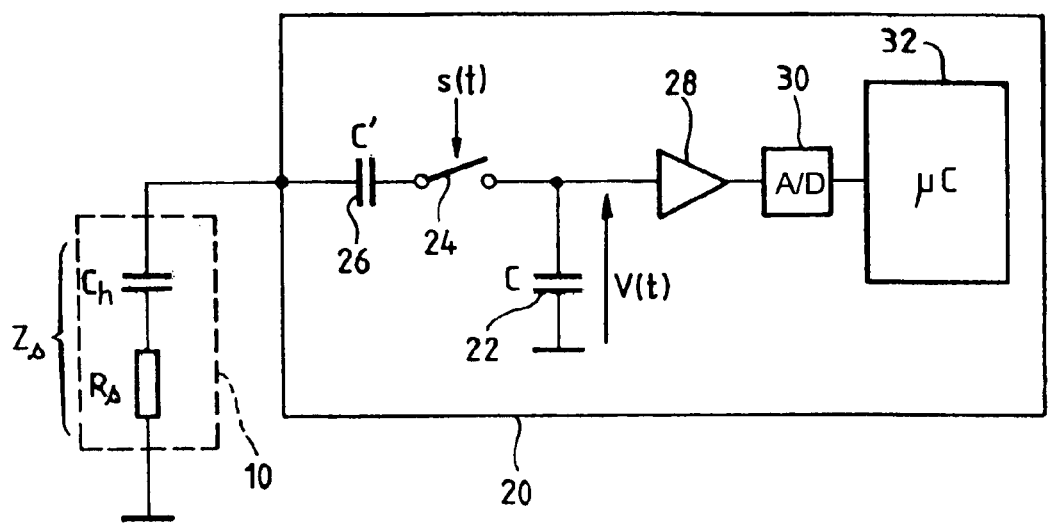
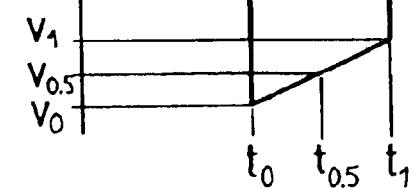
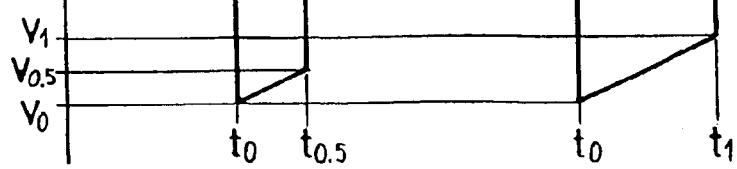

MEASUREMENT OF THE COMPLEX IMPEDANCE OF AN IMPLANTABLE LEAD

FIELD OF THE INVENTION

The present invention is directed to an "active implantable medical device" as such devices are defined by the Jun. 20, 1990 directive 90/385/CEE of the Council of the European Communities, and more particularly to pacemaker, defibrillator and/or cardiovertor devices able to deliver to the heart low energy pulses for the treatment of heartbeat rate disorders. The invention is not, however, limited to these particular devices, but also applies, as it will be understood, to any implantable medical device delivering electric stimuli to tissue by means of a conductor or a lead.

BACKGROUND OF THE INVENTION

The relevant active implanted medical devices typically comprise a generator containing the various electronic circuits and a power supply for the device. The generator is connected electrically and mechanically to a lead equipped with electrodes for the stimulation of tissue. Of particular interest are those devices that have leads equipped with electrodes for intracardiac stimulation, making it possible to detect the potentials of depolarization of the myocardium, and to deliver as needed the stimulation pulses produced by the generator.

An important parameter of an implanted lead is its impedance, because this parameter conditions the current necessary for stimulation (the lower the lead impedance, the higher the impedance of the electrode/myocardium interface) and, consequently, the lifespan of the implanted device.

The impedance is a parameter that can evolve over the course of time, because it depends not only on the intrinsic characteristics of the lead (geometry, materials, etc.) but also of the electric characteristics of the electrode/myocardium interface, that also can evolve over the course of time for various reasons, in particular the evolution of the environment of the tip of the lead (e.g., the formation of reactional contact tissue such as fibrin) and the deterioration of the conducting material forming the lead electrode.

It is thus important to be able to measure the impedance of the lead regularly, to determine whether this impedance remains within acceptable limits and, if required, to readjust the electric parameters of delivery of the stimulation pulse according to the value thus measured. This measurement is made difficult by the fact that the impedance of the lead is a complex impedance, having a pure resistive component and a capacitive component, components that can vary in different ways over the course of time.

The lead impedance Zs can be modeled by a pure resistance Rs in series with a capacitance Ch called "Helmholtz capacitance." The resistive component Rs is solely responsible for the current consumed with each stimulus, and the capacitive component Ch is, for its part, responsible for the loss by polarization to the electrode/myocardium interface.

The majority of the known implantable prostheses perform an evaluation of the complex impedance that amalgamates Rs and Ch, and that is also very imprecise and variable according to the measurement signal used: The value of the result provided by these apparatuses varies in particular according to the duration of the stimulation pulse.

The published international application WO-A-99/58192 proposes a process making it possible to determine separately the resistive and capacitance components to mitigate these disadvantages, but it requires a complex circuitry, putting in particular a shunt resistance in the stimulation circuit.

OBJECTS AND SUMMARY OF THE INVENTION

It is, therefore, an object of the present invention to propose a process for measuring the resistive component of the impedance of an implantable lead of a prosthesis independently of the capacitive component, which process is precise and reproducible, thus making it possible to determine with all the desired precision the current necessary for stimulation and, correlatively, to evaluate the probable lifespan of the prosthesis.

As it will be seen, the invention also allows, if it is wished, the determination of the capacitive component of the lead impedance (Helmholtz capacitance), independently of the resistive component. This parameter in particular makes it possible to evaluate the loss due to polarization, a problem that appears with the electrodes having a very small surface area (about 1.5 $mm^2$ or less). In this regard, the polarization problems that had existed with large surface area electrodes and were solved by changing to use of a granulose (porous) structure reappeared in tip electrodes having the same granulose structure but a small surface area. Large Helmholtz capacities are of no importance in practice.

To this end, the invention broadly provides a process that includes the stages of producing a stimulation pulse by the discharging of a storage capacitor on the lead of the device, where the storage capacitor was charged beforehand to a given voltage level; measuring the voltage variation at the terminals of the storage capacitor throughout the discharge; and determining the lead impedance based upon the voltage thus measured. An apparatus for implementing this process is also provided.

In a manner characteristic of the invention, the measurement stage includes sampling at least three successive values of the voltage at the terminals of the storage capacitor, and the impedance determining stage includes the separate determination of the resistive and/or capacitive components of the impedance of the lead from the aforesaid at least three sampled values of voltage thus obtained.

Very advantageously, the aforementioned determination is operated by an algebraic calculation, in particular by performing the voltage sampling at least three selected times so that the third time of sampling corresponds to twice the duration of the second time of sampling, with the first time of sampling being taken at the beginning of the stimulation pulse.

In a first preferred embodiment of the present invention, the aforementioned at least three successive values are sampled during the same stimulation pulse.

In a second preferred embodiment of the present invention, the aforementioned at least three successive values are sampled during at least two successive stimulation pulses, preferably produced so that one is twice duration of the other, the sampling times being selected at the beginning and the end of each of the two pulses.

BRIEF DESCRIPTION OF THE DRAWING

Further features, characteristics, and advantages of the present invention will appear to a person of ordinary skill in the art in view of the following detailed description of a preferred embodiment of the invention, made with reference to the drawings annexed, in which:

FIG. 1 is a schematic view of the various elements and circuits implied in the measurement of the lead impedance according to a preferred embodiment of the present invention;

FIG. 2 illustrates the profile of the stimulation pulse allowing the measurement of impedance according to a first embodiment of the process of the invention; and FIG. 3 illustrates the profile of the stimulation pulses used in a second embodiment of the process of the invention.

DETAILED DESCRIPTION OF THE INVENTION

As indicated at the beginning of description, from the electric point of view, lead 10 can be modeled by an impedance Zs made up of a pure resistance Rs in series with a connection capacitance Ch known as the Helmholtz capacitance. By convention, this lead impedance Zs also includes that of the conductor connecting the lead itself to generator 20, in particular the ohmic resistances of the circuit in addition to resistances of tissue.

The stimulation circuit includes, primarily, a tank-capacitor 22 of value C, a switch 24 controlled by a logical signal s(t), and a connection capacitor 26 of value C'. The capacitor 22 is charged by an appropriate circuit, not represented (in itself traditional and well-known in the art). The closing of the switch 24 causes the discharge of capacitor 22 and consequently the sending of a depolarization pulse to the lead and the myocardium. The measurement of impedance is operated by measurement of the voltage V(t) at the terminals of capacitor 22.

The measurement is carried out by use of a divider-sampler-blocker circuit 28 and an analog to digital (A/D) converter 30 able to deliver a digitized value of voltage to the microcontrollor 32. Circuit 28 is designed to modify the ratio of division according to the amplitude of the voltage stored in the capacitor 22, so as to scale the voltage to be in the analog input range of the analog to digital conversion capability of A/D converter 30. Microcontrollor 32 ensures the memorizing of the measured values of voltage, as well as performing calculations and memorizing the results thereof.

In an alternative embodiment, in particular if calculations are too complex and/or or too long, the microcontrollor 32 can transmit by telemetry the values measured and memorized to an external programmer to carry out necessary calculations.

The stimulation pulse takes the general form illustrated in FIG. 2. When at the moment $t_0$ the switch 24 is closed by the logical command s(t), the tank-capacitor 22 having a charge C discharges in a circuit having, in series, the switch 24, the connection capacitor C', the Helmholtz capacitance Ch and resistance Rs (the resistances in series of the switch and of the internal conductors, typically of a few ohms or a few tens of ohms at most, are taken into account in Rs. They are negligible in view of Rs: less than 1% of the Rs value).

The voltage V(t) at the terminals of the tank-capacitor 22 decreases, from the moment $t_0$ and until the moment $t_1$ of reopening of the switch 24, according to an exponential, traditional law of RC networks, given by the formula:

$$V(t) = \frac{V_0 * [C + C_s \exp\{-t/R_s * (1/C + 1/C_s)\}]}{C + C_s}$$

with $C_s = 1/(1/C' + 1/Ch)$, $V_0$ being the initial voltage at the terminals of capacitor 22.

In a manner characteristic of the invention, the voltage V(t) is sampled, then digitally converted in order to obtain three consecutive values of voltage: $V_0$ at the first time $t_0$, $V_{0.5}$ at the second time $t_{0.5}$ at midpoint of pulse, and $V_1$ at the at the third time $t_1$ corresponding at the end of the pulse. Starting from these values, it is possible by a calculation to obtain the values of the components of the lead impedance, given by the following:

$$R_s = \frac{-V_0 * t_1 * (V_0 - 2V_{0.5} + V_1)}{2 * C * L_n[(V_0 - V_1)/(V_0 - V_{0.5}) - 1] * (V_0 - V_{0.5})^2}$$

and $$Ch = \frac{C * C'}{C' * [((V_0 * V_1) - V_{0.5}^2)/(V_0 - V_{0.5})^2] - C}$$

the first time $t_0$ being selected as origin of time (i.e., the beginning of the pulse).

One will note that the choice, for the third time of sampling ($t_1$), which duration is twice the duration of the second time of sampling ($t_{0.5}$) makes it possible to give an analytical solution to the calculation. This advantageously provides an algebraic solution that avoids an iterative calculation that would be very difficult to realize, taking into account the limited resources in terms of computing power typically available within an implant (or even available in a remote programmer). Although preferred, it should be noted that the duration between the first and third times need not be precisely twice the duration between the first and second times, and other duration differences may be used.

An alternative embodiment in accordance with the present intention is illustrated in FIG. 3. Instead of carrying out the triple sampling during the same stimulation pulse, it is possible to use two consecutive stimulation pulses, for example, pulses of the same amplitude but with one pulse having twice the duration of the other, by sampling for each pulse the value of voltage at the terminals of the tank-capacitor 22 at the beginning and the end of the respective pulses. Preferably, the shortest duration pulse is the first, because the discharge of the capacitor 22 is thus less.

The embodiment in accordance with this alternative is certainly a little less precise, for it presupposes that the initial stimulation voltage $V_0$ is exactly the same for the two pulses. However, it has an offsetting advantage in that it is simpler to realize and does not require a means of calculation (microprocessor or microcontroller) as fast as that required for the first embodiment using a single stimulation pulse.

It will be appreciated by a person of ordinary skill in the art that the present invention, described in the context of a unipolar lead configuration, also applies of course, mutatis-mutandis, to a bipolar lead configuration. One will note in this regard that, in a bipolar configuration, the modeled Helmholtz capacitance Ch is the sum of capacities corresponding to the two electrodes, proximal and distal, and that the proximal electrode capacitance is much higher than the distal electrode, taking into account the annular form and greater surface area of the proximal electrode.

It should be understood that the present invention is preferably implemented in software of a microprocessor controlled implantable medical device that is programmable to charge and discharge a tank-storage capacitor to deliver the desired stimulation pulse(s), and to monitor the discharge voltages. Advantageously, the present invention can be downloaded to an already implanted device by an external programmer, in a conventional manner, as software instructions to modify the operation of the already implanted device, for such devices that are able to receive software instructions and to modify its operation in response thereto. Such suitable devices include the Chorus™ and Talent™ brand pacemaker devices and the Defender™ brand defibrillator devices, available from Ela Medical, Montrouge France.

One skilled in the art also will appreciate that the present invention can be implemented by embodiments other that the particular embodiments disclosed, which are presented for purposes of illustration, and not of limitation.

I claim:

1. A process for measuring the complex impedance of a lead of an active implantable medical device, in particular a pacemaker, a defibrillator and/or a cardiovertor, having a tank capacitor, the tank capacitor having terminals for discharging a stimulation pulse, comprising:

discharging the tank capacitor to produce a stimulation pulse on the lead;

measuring a voltage variation (V(t)) at the terminals of the tank-capacitor during said discharge; and determining a lead impedance (Zs) based upon the measured voltage, wherein:

the step of measuring comprises sampling at least three successive values of the voltage at the terminals of the tank capacitor, and the step of determining comprises determining separately a resistive component (Rs) and a capacitive component (Ch) of the impedance of the lead from said at least three sampled values of voltage; and wherein said determination is operated by an algebraic calculation; and said sampling comprises sampling a first time, a second time, and a third time, wherein the time of the third time of sampling corresponds to twice the duration between the second time and the first time, and wherein the first time is at the beginning of the stimulation pulse.

2. The process of claim 1, wherein sampling said at least three successive values further comprises sampling said at least three successive values during the same stimulation pulse.

3. The process of claim 1, wherein sampling said at least three successive values further comprises sampling said at least three successive values during two successive stimulation pulses.

4. The process of claim 3, further comprising providing two successive stimulation pulses including a first pulse followed by a second pulse with one pulse having twice the duration of the other pulse, wherein sampling said at least three successive values further comprises sampling a first time at the beginning of said first pulse, a second time at the end of the first pulse and a third time at the end of the second pulse.

5. In an active implantable medical device such as a pacemaker, a defibrillator and/or a cardiovertor, including a tank capacitor, the tank capacitor having terminals for discharging a stimulation pulse, and a circuit for measuring the complex impedance of a lead including:

means for discharging the tank-capacitor on the lead to produce a stimulation pulse;

means for measuring a voltage variation (V(t)) at the terminals of the tank-capacitor during said discharge; and means for determining a lead impedance (Zs) based upon the voltage thus measured, wherein the improvement comprises:

means for sampling at least three successive values of the voltage at the terminals of the tank capacitor; and means for determining separately a resistive component (Rs) and a capacitive component (Ch) of the impedance of the lead from said at least three sampled values of voltage; and wherein said determination means comprises an algebraic calculation, and said sampling means further comprises means for sampling a first time, a second time, and a third time, wherein the time of the third time of sampling corresponds to twice the duration between the second time and the first time, and wherein the first time is at the beginning of the stimulation pulse.

6. The device of claim 5, wherein said sampling means further comprises means for sampling said at least three successive values during the same stimulation pulse.

7. The device of claim 5, wherein said sampling means further comprises means for sampling said at least three successive values during at least two successive stimulation pulses.

8. The device of claim 7, further comprising means for providing two successive stimulation pulses including a first pulse followed by a second pulse, with one pulse having twice the duration of the other pulse, wherein said sampling means further comprises means for sampling a first time at the beginning of said first pulse, a second time at the end of the first pulse and a third time at the end of the second pulse.

* * * * *